(12) United States Patent
Woltering

(10) Patent No.: US 7,381,400 B2
(45) Date of Patent: Jun. 3, 2008

(54) INJECTION OF A RADIOACTIVE DYE FOR SENTINEL LYMPH NODE IDENTIFICATION

(75) Inventor: Eugene A. Woltering, Kenner, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 510 days.

(21) Appl. No.: 10/890,420

(22) Filed: Jul. 13, 2004

(65) Prior Publication Data

US 2006/0013768 A1 Jan. 19, 2006

(51) Int. Cl.
*A61K 49/00* (2006.01)

(52) U.S. Cl. .................. 424/9.1; 424/1.11; 424/1.65; 424/1.81; 424/1.85; 424/1.89

(58) Field of Classification Search ............... 424/1.11, 424/1.65, 1.81, 1.85, 1.89, 9.1, 9.2, 9.3, 9.4, 424/9.5, 9.6, 9.7, 9.8
See application file for complete search history.

(56) References Cited

U.S. PATENT DOCUMENTS

| 4,782,840 | A | 11/1988 | Martin, Jr. et al. ......... 600/431 |
| 5,008,546 | A | 4/1991 | Mazziotta et al. .......... 250/366 |
| 6,409,990 | B1 | 6/2002 | Vera ......................... 424/9.35 |
| 2006/0002850 | A1* | 1/2006 | Maloney et al. ............ 424/1.11 |

FOREIGN PATENT DOCUMENTS

| WO | WO 00/74727 | 12/2000 |
| WO | WO 2004/016154 | 2/2004 |

OTHER PUBLICATIONS

Link et al (Cancer Research, 1992, vol. 52, No. 16, pp. 4385-4390).*

Tsopelas, C. et al., "Visualization of Lynmphatic Flow in a Rabbit Model Using Six New $^{99m}$Tc-Labeled Dyes," abs., Hellenic J. of Nuclear Med., vol. 2, pp. 96-202 (2000).

Tsopelas, C. et al., "Why Certain Dyes are Useful for Localizing the Sentinel Lymph Node," The J. Of Nuclear Med., vol. 43, n. 10, pp. 1377-1382 (2002).

Sutton, R. et al., "Sentinel Node Biopsy and Lymphoscintigraphy With a Technetium 99m Labeled Blue Dye in a Rabbit Model," Surgery, vol. 131, n. 1, pp. 44-49 (2002).

Blower, P.J. et al., "123l-methylene blue: an unsatisfactory parathyroid imaging agent," Nuclear Medicine Comms., vol. 13, pp. 522-527 (1992).

Cascinelli, N. et al., "Sentinel lymph node biopsy in cutaneous melanoma: The WHO Melanoma Program Experience," Ann. Surg. Oncol., vol. 7, pp. 469-474 (2000).

Echt, M.L. et al., "Detection of sentinel lymph nodes with lymphazurin in cervical, uterine, and vulvar malignancies," Southern Medical Journal, vol. 92, pp. 204-208 (1999).

Hayashi, H. et al., "Sentinel lymph node mapping for gastric cancer using a dual procedure with dye- and gamma probe-guided techniques," J. Am. Coll. Surg., vol. 196, pp. 68-74 (2003).

Link, E.M. et al., "Early detection of melanoma metastases with radioiodinated methylene blue," Eur. J. Nucl. Med., vol. 25, pp. 1322-1329 (1998).

Link, E.M., "Targeting melanoma with $^{211}$At/$^{131}$I-methylene blue: preclinical and clinical experience," Hybridoma, vol. 18, pp. 77-82 (1999).

Link, E.M. et al., "Uptake and therapeutic effectiveness of $^{125}$I- and $^{211}$At-methylene blue for pigmented melanoma in an animal model system," Cancer Res., vol. 49, pp. 4332-4337 (1989).

McMasters, K.M. et al., "Sentinel lymph node biopsy for melanoma: How many radioactive nodes should be removed?" Ann. Surg. Oncol., vol. 8, pp. 192-197 (2001).

Miner, T.J. et al., "Guidelines for the safe use of radioactive materials during localization and resection of the sentinel lymph node," Ann. Surg. Oncol., vol. 6, pp. 75-82 (1999).

(Continued)

*Primary Examiner*—Dameron L. Jones
(74) *Attorney, Agent, or Firm*—John H. Runnels; Bonnie J. Davis

(57) ABSTRACT

A one-step procedure for sentinel lymph node identification and biopsy using a single compound, a radiolabeled, low molecular weight dye (e.g., $^{125}$I-labeled methylene blue). This radiolabed dye is mixed with an unlabeled, similar molecular weight dye (e.g., isosulfan or methylene blue). The mixture is injected at the time of surgery, and rapidly migrates to reach the lymph nodes in less than 20 min, more preferably in less than 15 min and most preferably in less than 10 min. Using rabbits, rapid transit of $^{125}$I-methylene blue to regional lymph nodes with limited systemic biodistribution has been confirmed. By admixing small amounts of radiolabeled dye with a large amount of unlabeled dye, the sentinel lymph node identification was similar to that for the prior two-step dual mapping process, but with enhanced SLN localization because of the lower energy gamma emission of $^{125}$I as compared with $^{99m}$Tc.

22 Claims, 8 Drawing Sheets

OTHER PUBLICATIONS

Moffat, F.L., Jr., et al., "Unfiltered sulfur colloid and sentinel node biopsy for breast cancer: Technical and kinetic considerations," Ann. Surg. Oncol., vol. 6, pp. 746-755 (1999).

Raffaelli, A. et al., "Investigation on the iodination reaction of methylene blue by liquid chromatography-mass spectrometry with ionspray ionization," Journal of Chromatography A, vol. 854, pp. 57-67 (1999).

Saha, S. et al., "Lymphazurin 1% versus $^{99m}$Tc sulfur colloid for lymphatic mapping in colorectal tumors: a comparative analysis," Ann. Surg. Oncol., vol. 11, pp. 21-26 (2004).

Schwartz, G.F. et al., "Proceedings of the consensus conference on the role of sentinel lymph node biopsy in carcinoma of the breast, Apr. 19-22, 2001, Philadelphia, PA, USA," The Breast Journal, vol. 8, pp. 126-138 (2002).

Simmons, R. et al., "Methylene blue dye as an alternative to isosulfan blue dye for sentinel lymph node localization," Ann. Surg. Oncol., vol. 10, pp. 242-247 (2003).

Tuttle, T.M. "Technical advances in sentinel lymph node biopsy for breast cancer," Am. Surg., vol. 70, pp. 407-413 (2004); and International Application No. WO 00/74727.

* cited by examiner

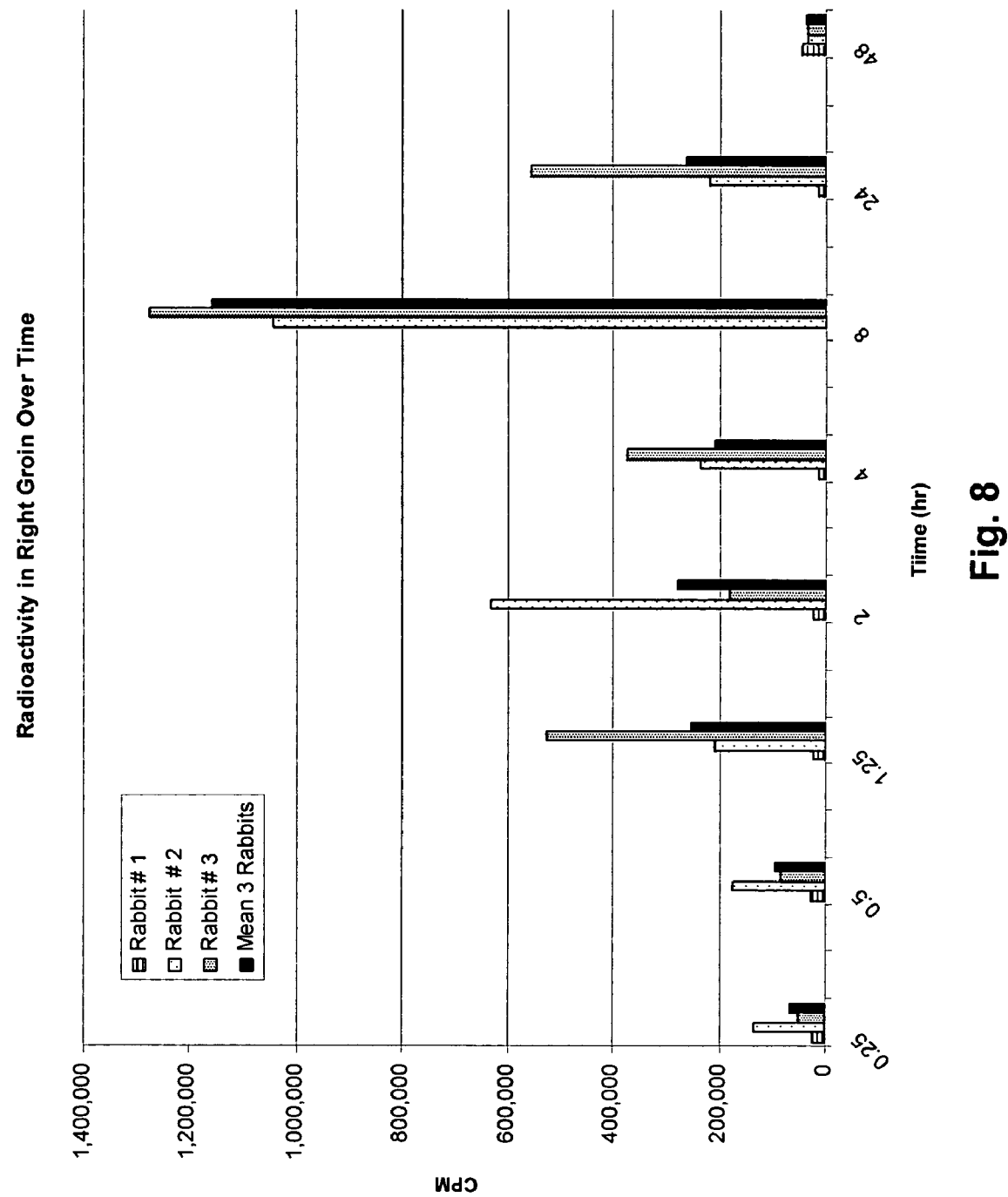

INJECTION OF A RADIOACTIVE DYE FOR SENTINEL LYMPH NODE IDENTIFICATION

The development of this invention was subject to a contract between the Board of Supervisors of Louisiana State University and Agricultural and Mechanical College, and the United States Department of Veterans Affairs. The Government has certain rights in this invention.

This invention pertains to a method to identify sentinel lymph node(s), node(s) that receive lymphatic fluid from a tumor tissue, by injecting into or around a tumor tissue during surgery a single active compound, a radiolabeled dye, that rapidly travels to the sentinel lymph node(s).

One of the major techniques for determining the prognosis of a cancer involves determining whether the cancer has metastasized into other areas of the body. As lymphatic fluid flows from various areas of the body, the fluid flows through lymph channels and then into lymph nodes where it is filtered. The initial spread of most solid tumors occurs as metastasizing cells move into the lymph channels, and then are filtered by the lymph nodes. The first lymph node that is reached by the lymphatic fluid from the tumor region is called the sentinel lymph node ("SLN"). See T. J. Miner et al., "Guidelines for the safe use of radioactive materials during localization and resection of the sentinel lymph node," Ann. Surg. Oncol., vol. 6, pp. 75-82 (1999). For example, the sentinel lymph nodes for breast tumors are usually found in the axilla, or armpit, of the patient. A tumor may have one or more sentinel lymph nodes.

A sentinel lymph node biopsy is used to determine whether all lymph nodes in the drainage area must be removed or only the SLN(s) are removed. This procedure depends upon an effective technique for identifying the sentinel lymph node(s) for a tumor. If the cancer has spread to the lymph nodes, the sentinel lymph node should be positive (i.e., cancerous), and the surgeon will then remove all lymph nodes in the region. If the SLN is pathologically negative, all other nodes of the same area are generally cancer-free. See N. Cascinelli et al., "Sentinel lymph node biopsy in cutaneous melanoma: The WHO Melanoma Program Experience," Ann. Surg. Oncol., vol. 7, pp. 469-474 (2000). Thus, if the SLN is pathologically negative, the patient has lost only the SNL. Accurate identification and biopsy of the sentinel lymph node (when pathologically negative) means that other nodes (non-SLNs) are retained by the patient. The retention of normal lymph nodes benefits the patient by preventing lymphatic fluid accumulation in the arm or other extremity.

The current techniques for identifying the sentinel lymph node(s) involve the use of a radioactive colloid compound, a vital dye, or both. For example, a blue dye is injected around the tumor during surgery and visually stains the sentinel node(s) within 5 to 10 min. See International Patent Application No. 2004/016154. The blue dye conventionally used for this sentinel lymph node procedure is an isosulfan blue dye (e.g., Lymphazurin™). A radioactive colloid, if used, is usually injected 2 to 24 hr before surgery. See G. F. Schwartz et al., "Proceedings of the consensus conference on the role of sentinel lymph node biopsy in carcinoma of the breast, Apr. 19-22, 2001, Philadelphia, Pa., USA," The Breast Journal, vol. 8, pp. 126-138 (2002). The radiolabeled colloid enables the site of the sentinel node(s) to be remotely detected both by preoperative lymphoscintigraphy and by intraoperative handheld gamma probe detection. The radioactive colloid compound is usually a technetium-sulfur colloid (e.g., $^{99m}$Tc-sulfur colloid, Mallinckrodt, St. Louis, Mo.). Unfiltered $^{99m}$Tc-sulfur colloid is often used because its large particle size slows migration, and makes it less likely that the radioactive material will migrate through the initial sentinel lymph node and into second and third echelon nodes before detection. A particle size of 5 nm has been reported as optimal for the radioactive compound. Unfiltered $^{99m}$Tc-sulfur colloid has been reported not to pass beyond the sentinel lymph nodes for at least the first six hours after injection. See F. L. Moffat, Jr., et al., "Unfiltered sulfur colloid and sentinel node biopsy for breast cancer: Technical and kinetic considerations," Ann. Surg. Oncol., vol. 6, pp. 746-755 (1999); and International Application No. WO 00/74727.

When both a dye and a radiolabeled substance are used, they have been injected separately, the radiolabeled substance before the surgery and the dye during surgery. Both substances are usually injected in or near the tumor or tumor site and flow through the lymphatic channels to the sentinel lymph node draining that site. The SLN can be located preoperatively by lymphoscintigraphy, and during surgery both by detecting the emissions from the radioactive substance and by visual inspection of nodes that are colored by the dye. See Cascinelli, 2000; and K. M. McMasters et al., "Sentinel lymph node biopsy for melanoma: How many radioactive nodes should be removed?" Ann. Surg. Oncol., vol. 8, pp. 192-197 (2001). Literally hundreds of studies have appeared in the scientific literature validating the use of sentinel lymph node biopsy as an accurate method to evaluate the risk of metastatic disease in auxiliary nodes. Sentinel lymph node biopsy has been effectively used or proposed in several solid tumor types, including melanoma, breast cancer, head and neck cancer, lung cancer, bladder cancer, neuroendocrine cancer, squamous carcinoma, prostate cancer, gastric cancer, cervical cancer, vulvar cancer, thyroid cancer, pancreatic cancer, head and neck cancer, renal cancer, esophageal cancer, rectal cancer, penile cancer, lymphoma, multiple myloma, Merkel cell tumors, ovarian cancer, and colorectal cancer. See M. L. Echt et al., "Detection of sentinel lymph nodes with lymphazurin in cervical, uterine, and vulvar malignancies," Southern Medical Journal, vol. 92, pp. 204-208 (1999); H. Hayashi et al., "Sentinel lymph node mapping for gastric cancer using a dual procedure with dye- and gamma probe-guided techniques," J. Am. Coll. Surg., vol. 196, pp. 68-74 (2003); S. Saha et al., "Lymphazurin 1% versus $^{99m}$Tc sulfur colloid for lymphatic mapping in colorectal tumors: a comparative analysis," Ann. Surg. Oncol., vol. 11, pp. 21-26 (2004); and International Publication No. WO 2004/016154. These reports document the success of sentinel node localization, usually using isosulfan blue dye, with or without also using a technetium 99-labeled sulfur colloid. Later reports indicate an improved accuracy at identifying the sentinel lymph node by using both dye and radioactive colloid. See Schwartz et al., 2002.

Recently several reports have appeared suggesting that sentinel node identification accuracy and yield could be duplicated with the use of methylene blue dye (3,7-bis(dimethylamino)phenothiazine-5-ium chloride) instead of isosulfan blue dye. See R. Simmons et al., "Methylene blue dye as an alternative to isosulfan blue dye for sentinel lymph node localization," Ann. Surg. Oncol., vol. 10, pp. 242-247 (2003). A change in dye preference has accordingly also found its way into the practice of many surgeons since methylene blue is less expensive and more readily available than the commonly used isosulfan blue dye, Lymphazurin™. Small quantities (usually about 4 to 5 cc) of methylene blue are injected into the tumor region. Methylene blue has not been associated with reported adverse events.

Sentinel node biopsy using radioactive colloid has some unanticipated consequences for both surgeon and patient. Patients usually undergo a separate procedure for injecting the radioactive colloid prior to cancer surgery. This procedure is carried out either the afternoon prior to surgery or the morning of surgery. The patient can then be screened before the surgery by lymphoscintigraphy. The injection of radioactive colloid is unusually painful, whether it is injected in small quantities intradermally or in larger quantities around the tumor. With the increasing demand for sentinel lymph node sampling, surgeons have been forced to deal with major delays in surgical schedules. Although some surgeons have injected the radioactive colloid at the time of surgery to avoid preoperative lymphoscintigraphy, they must still wait 30 to 60 min for the radioactive colloid to reach the lymph nodes. See T. M. Tuttle, "Technical advances in sentinel lymph node biopsy for breast cancer," Am. Surg., vol. 70, pp. 407-413 (2004); and International Application No. WO 00/74727.

Other shortcomings of the known procedures include a relatively insensitive degree of localization, i.e., the inability to discriminate nodes on a fine scale. $^{99m}$Tc has high-energy gamma emissions. A significant amount of activity (10 mCi) must be injected to ensure adequate node uptake. A large compound, e.g., colloid, is used to slow loss of radioactivity from the lymph nodes. However, some of the activity must clear from the injection site (especially ones close to the axilla) before using a handheld gamma probe in the axilla, or the gamma detector will be "swamped," making it difficulty to distinguish a small radioactive sentinel node from a non-radioactive neighboring node.

Radioactive iodine-labeled methylene blue has previously been used for the early diagnosis and treatment of melanoma metastases. Methylene blue is used because it possesses a high affinity for melanin and accumulates preferentially in melanoma cells with high concentrations of melanin. See A. Raffaelli et al., "Investigation on the iodination reaction of methylene blue by liquid chromatography-mass spectrometry with ionspray ionization," Journal of Chromatography A, vol. 854, pp. 57-67 (1999); E. M. Link, "Targeting melanoma with $^{211}$At/$^{131}$I-methylene blue: preclinical and clinical experience," Hybridoma, vol. 18, pp. 77-82 (1999); E. M. Link et al., "Early detection of melanoma metastases with radioiodinated methylene blue," Eur. J. Nucl. Med., vol. 25, pp. 1322-1329 (1998); and E. M. Link et al., "Uptake and therapeutic effectiveness of $^{125}$I- and $^{211}$At-methylene blue for pigmented melanoma in an animal model system," Cancer Res., vol. 49, pp. 4332-7 (1989). Early research on use of $^{123}$I-labeled methylene blue to image and localize parathyroid adenomas proved unsatisfactory. See P. J. Blower et al., "$^{123}$I-methylene blue: an unsatisfactory parathyroid imaging agent," Nuclear Medicine Comms., vol. 13, pp. 522-527 (1992).

International Publication No. WO 2004/016154 discloses the use of a marker nucleic acid segment to aid in sentinel lymph node biopsy.

International Publication No. WO 00/74727 discloses the co-injection of a visible blue dye with a radiopharmaceutical agent (comprising a probe with a radiolabel) for lymphoscintigraphy. It discloses linking the dye to a probe that is radiolabeled, e.g., isothiocyanate to $^{99m}$Tc sulfur colloid, and the importance of size of the radiopharmaceutical agent. The list of probes include molecules of large molecular weight (e.g., colloids, starch, dextran, albumin, etc.) to achieve an optimal size of 5 nm. The minimum detection time after injection was 30 min.

I have invented a one-step procedure for sentinel lymph node biopsy using a radiolabeled, low molecular weight dye (e.g., $^{125}$I-labeled methylene blue). This radiolabled dye is preferably mixed with an unlabeled, similar molecular weight dye (e.g., isosulfan or methylene blue) of sufficient amount to enhance visual location of the lymph node(s). The unlabeled dye may be an otherwise identical compound without the radiolabel. The mixture is injected at the time of surgery, and rapidly migrates to reach the lymph nodes in less that 20 min, more preferably in less than 15 min, and most preferably in less than 10 min. Using rabbits, rapid transit of $^{125}$I-methylene blue to regional lymph nodes with limited systemic biodistribution has been confirmed. By admixing small amounts of radiolabeled dye (e.g., from about 0.1 cc to about 0.5 cc) with a large amount of unlabeled dye (e.g., from about 2 cc to about 10 cc, preferably about 4 to 5 cc), the sentinel lymph node identification was similar to the prior two-step dual mapping process, but with enhanced SLN localization because of the lower energy gamma emission of $^{125}$I as compared with $^{99m}$Tc.

BRIEF DESCRIPTION OF DRAWINGS

FIG. 8 illustrates the radioactivity measured in the right groin region at several time periods after injection of $^{125}$I-methylene blue for each of three rabbits and an average of the three rabbits.

Figure 1:
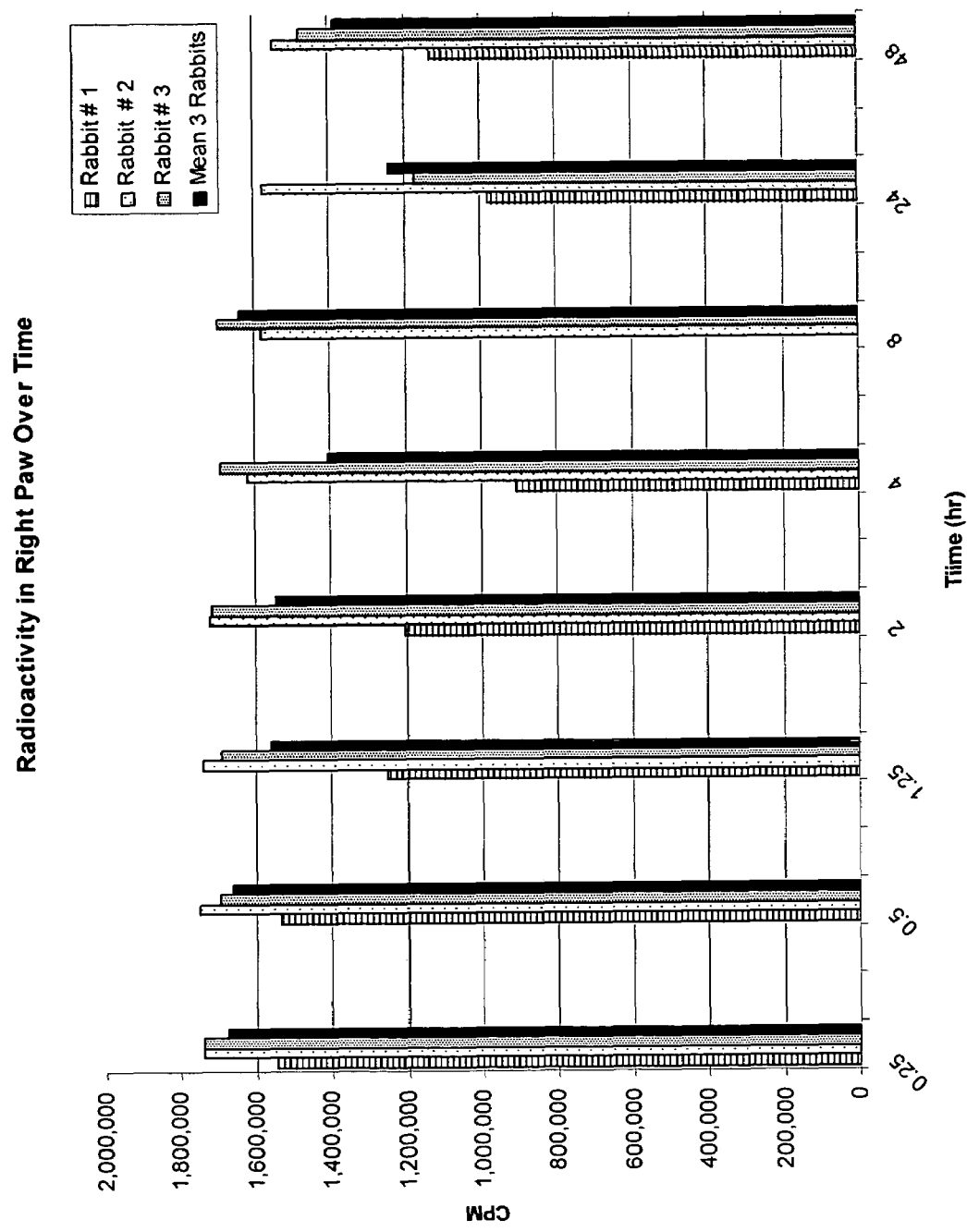
FIG. 1 illustrates the radioactivity measured in the right paw at several time periods after injection of $^{125}$I-methylene blue for each of three rabbits, and an average of the three rabbits.

Several dyes may be used to visualize the lymph nodes. The dye may, for example, be a nonfluorescent dye, a fluorescent dye, an ultraviolet fluorescent dye, a visible fluorescent dye, and infrared fluorescent dye, a chemiluminescent dye, a phosphorescent dye, or a bioluminescent dye. The dye preferably has the following properties: (1) a small molecule (molecular weight less than about 2000) that is non-toxic, non-pyrogenic, and that can be sterilized; (2) a molecule that can be either radiolabeled directly or chelated to a radioisotope; and (3) a molecule that will be transported rapidly through the lymph channels to the lymph node(s). Examples of low molecular weight dyes that are useful in this invention include isosulfan blue (molecular weight, 566.70), patent blue dye (e.g., Patent Blue-V), methylene blue (molecular weight, 319.85), tartrazine (molecular weight, 534.39), iodocyanine green (molecular weight, 774.99), rose Bengal (molecular weight, 1049.84), congo red (molecular weight, 696.76), fluorescein (molecular weight, 332.30) and their respective derivatives. A list of potential dyes useful for this technology is disclosed for example in International Publication Nos. WO 00/74727 and WO 2004/016154, the disclosures of both of which are expressly incorporated by reference. The size of the radiolabeled dye should be small enough that the compound travels from the site of injection near the tumor to the sentinel lymph node in less than about 20 min, more preferably in less than about 15 min, and most preferably in less than about 10 min. This small size requirement for the radiolabeled compound is in stark contrast to prior references that recommend an optimal particle size of about 5 nm, specifically to slow the migration of the radiolabeled colloid compound.

Examples of radiolabels that are useful in this invention include radioisotopes that can be directly attached to the dye or chelated to the dye molecule and that can be detected using a handheld probe during surgery. Isotopes that emit gamma or x-rays are especially useful, although radioisotopes emitting beta particles (electrons or positrons), or alpha particles could be useful depending on the type of probe available. Examples of elements whose radioisotopes might be used include, but is not limited to, the following: Tc, Re, Mn, Fe, Co, Ni, Zn, Cd, Se, Mo, W, Cu, Ag, Au, Tl, Hg, Cr, Rh, B, I, Cl, F, At, Y, Lu, Gd, Ga, Ho, In, Sm and Yb. In addition, the most preferred isotope is one with detectable radiation that readily can be specifically localized by a radiation detection probe placed adjacent to the lymph node. As specific localization is the goal, the preferred isotopes are those that decay via small energy transitions (30 to 300 keV) and have highly localized dose profiles. For gamma and x-ray emitters, preferred isotopes emit photons with energies less than about 300 keV, more preferred less than about 150 keV, and most preferred less than about 50 keV, e.g., $^{125}$I. Other low energy isotopes include $^{111}$In, $^{75}$Se, and $^{57}$Co. See U.S. Pat. No. 4,782,840. Radioisotopes emitting beta particles (e.g., $^{124}$I, $^{90}$Y, 18F, and $^{68}$Ga) additionally can be used in conjunction with a probe that can detect either beta electrons or positrons. The detection of beta radiation intraoperatively is disclosed, for example, in U.S. Pat. No. 5,008,546, the disclosure of which is incorporated herein by reference. Isotopes that emit higher energy particles (e.g., $^{131}$I) may also be used, although suitable collimation of the radiation detection probe must be employed, which may impede the instrument being facile to the surgeon and may limit the areas within the body cavity that can be suitably surveyed. Other isotopes that might be used include $^{123}$I, $^{124}$I, $^{99m}$Tc, $^{169}$Yb, $^{186}$Re, $^{188}$Re, $^{211}$At, $^{77}$Br, $^{67}$Ga, $^{86}$Y, $^{193}$Pt, $^{195m}$Pt, and $^{201}$Tl. The optimal combination of isotope and probe will allow localization of a node with a resolution less than 1 cm, preferably less than 1 mm.

The ratio of radiolabeled dye to unlabeled dye depends on the isotope and sensitivity of the probe. The total amount of dye, both labeled and unlabeled, must be sufficient to visually see the lymph channels and lymph nodes. The amount usually recommended is about 4 cc to about 5 cc. The amount of the radiolabeled dye should be sufficient that a SNL will have enough radioactivity to be detected by a hand held probe to be clearly distinct from background radioactivity.

The radiolabeled dye can be used to identify sentinel lymph node(s) of any solid tumor that is known to metastasize, including melanoma, breast cancer, head and neck cancer, lung cancer, bladder cancer, neuroendocrine cancer, squamous carcinoma, prostate cancer, gastric cancer, cervical cancer, vulvar cancer, thyroid cancer, pancreatic cancer, head and neck cancer, renal cancer, esophageal cancer, rectal cancer, penile cancer, lymphoma, multiple myloma, Merkel cell tumors, ovarian cancer, and colorectal cancer.

EXAMPLE 1

Time-Line and Distribution of Radiolabeled Methylene Blue

To determine the time line and distribution for a radiolabeled dye, twenty-four rabbits of mixed ages and sex were injected at the same time. The animals were injected with 1 ml $^{125}$I-methylene blue (1 mCi/ml; $^{125}$I-3,7-bisdimethylaminophenazathionine; ISO-Tex Diagnostics, Inc., Friendswood, Tex.), a radiolabeled iodine salt of methylene blue, in the right hind paw. Groups of three animals were sacrificed at eight time periods: 0.25 hr, 0.5 hr, 1.25 hr, 2 hr, 4 hr, 8 hr, 24 hr, and 48 hr. At each of these times the rabbits underwent dissection by three researchers working in parallel. Additionally, radioactivity in the lymph nodes was monitored using two different Neoprobe model 1000 handheld gamma probes. The rabbits were dissected to find the popliteal fossa, the nodes that were radioactive emitters, and the nodes with blue coloration. The overall biodistribution of radioactivity was determined by monitoring the following tissues: heart, liver, lung, stomach, intestine, kidneys-adrenals (combined), spleen, testes or ovaries, thyroid, overall carcass, and blood. Dissected tissue that was presumed to be a lymph node was verified as a lymph node by fixing the tissue in formalin for later histological sectioning and analysis.

Radioactivity was monitored using two Neoprobes (Model 1000, Neoprobe Corp., Dublin, Ohio). The readings were converted to counts per minute (CPM). Three readings were taken for each rabbit at each time point, and were averaged. The average for three rabbits at each time point was calculated for each time period. Background levels were determined over the base of the neck.

Figure 2:
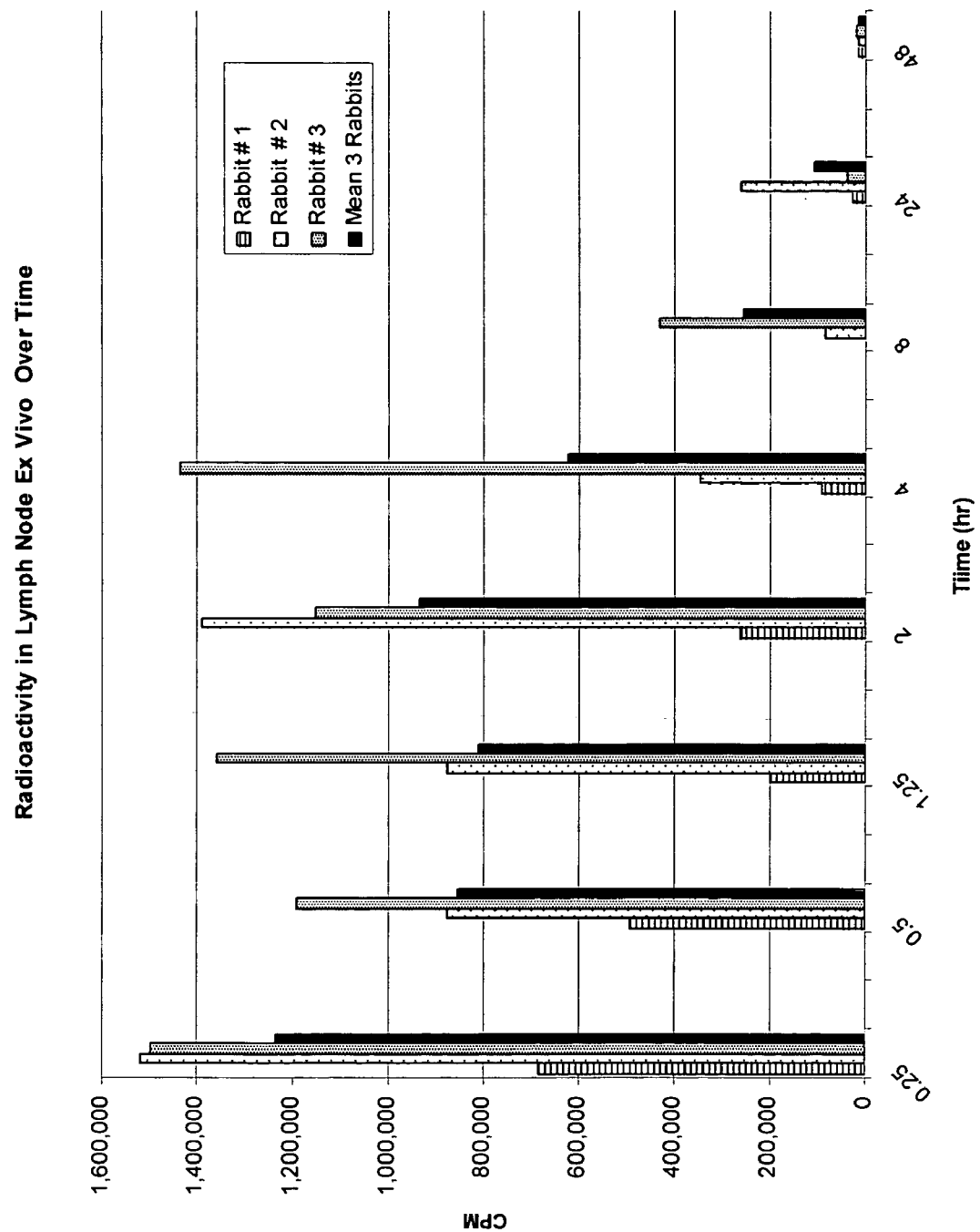
FIG. 2 illustrates the radioactivity measured in vivo in the sentinel lymph node at several time periods after injection of $^{125}$I-methylene blue for each of three rabbits, and an average of the three rabbits.
Figure 3:
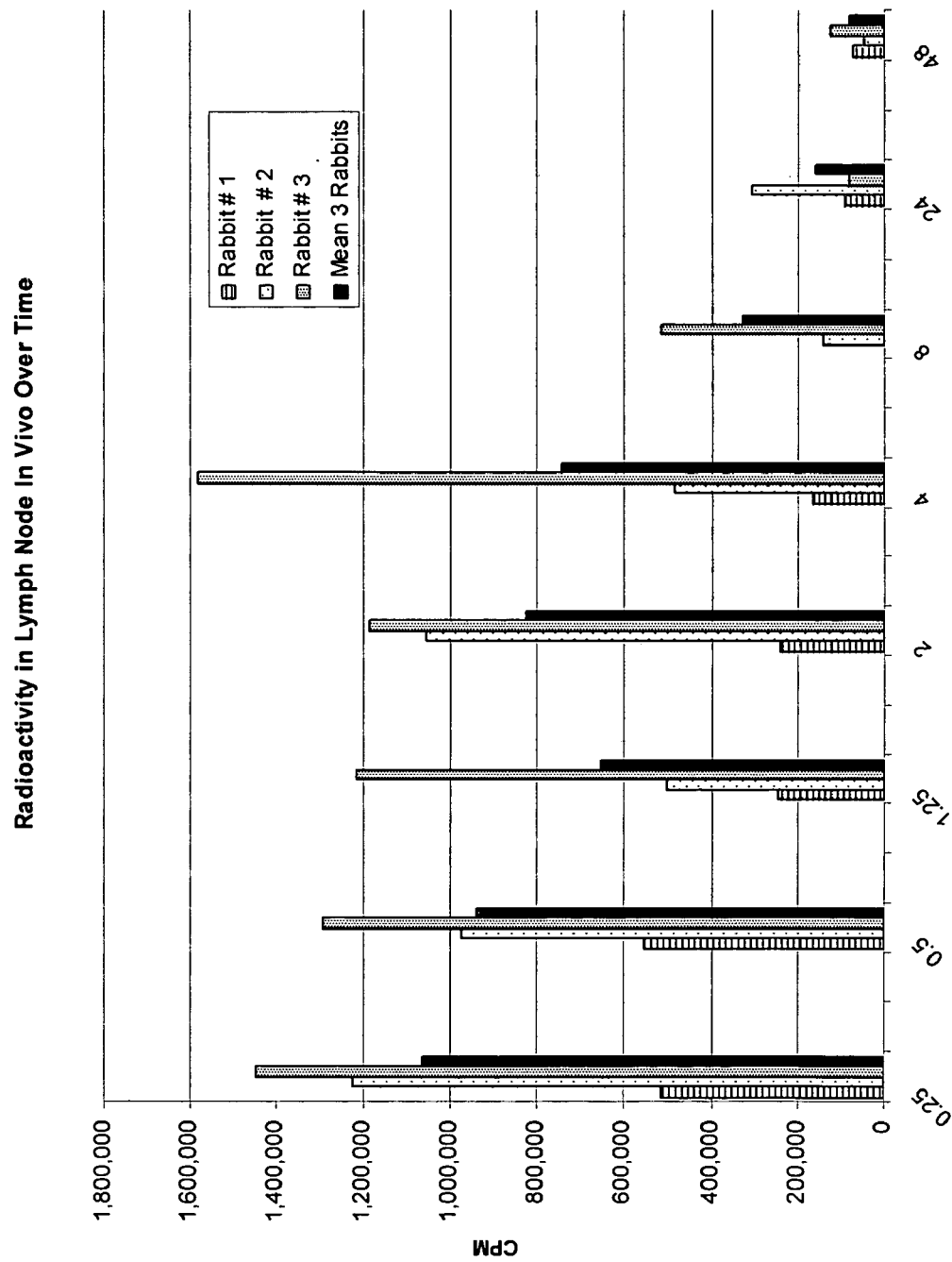
FIG. 3 illustrates the radioactivity measured in vitro in the sentinel lymph node at several time periods after injection of $^{125}$I-methylene blue for each of three rabbits, and an average of the three rabbits.
Figure 4:
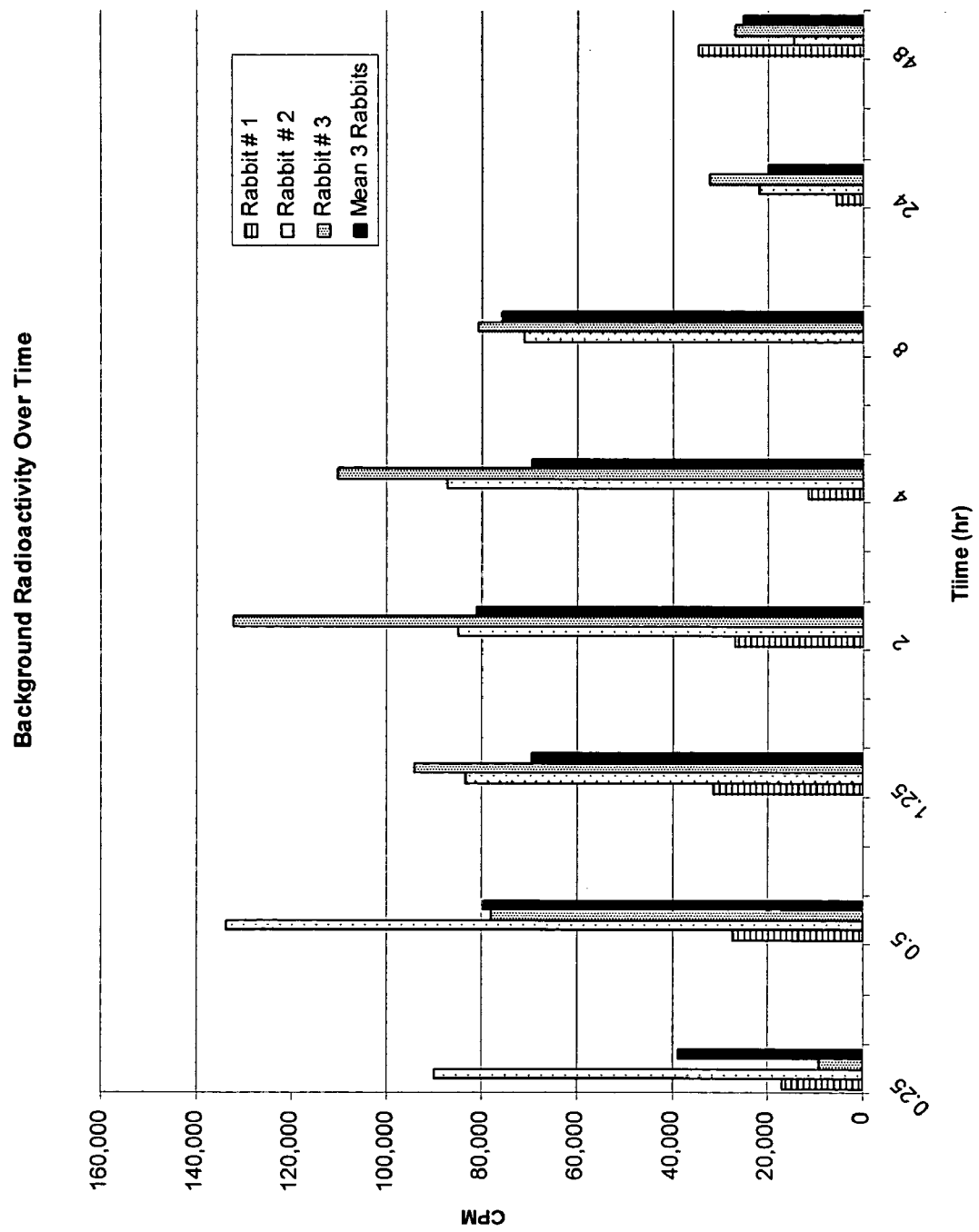
FIG. 4 illustrates the radioactivity measured in the neck (the background radioactivity) at several time periods after injection of $^{125}$I-methylene blue for each of three rabbits, and an average of the three rabbits.
Figure 5:
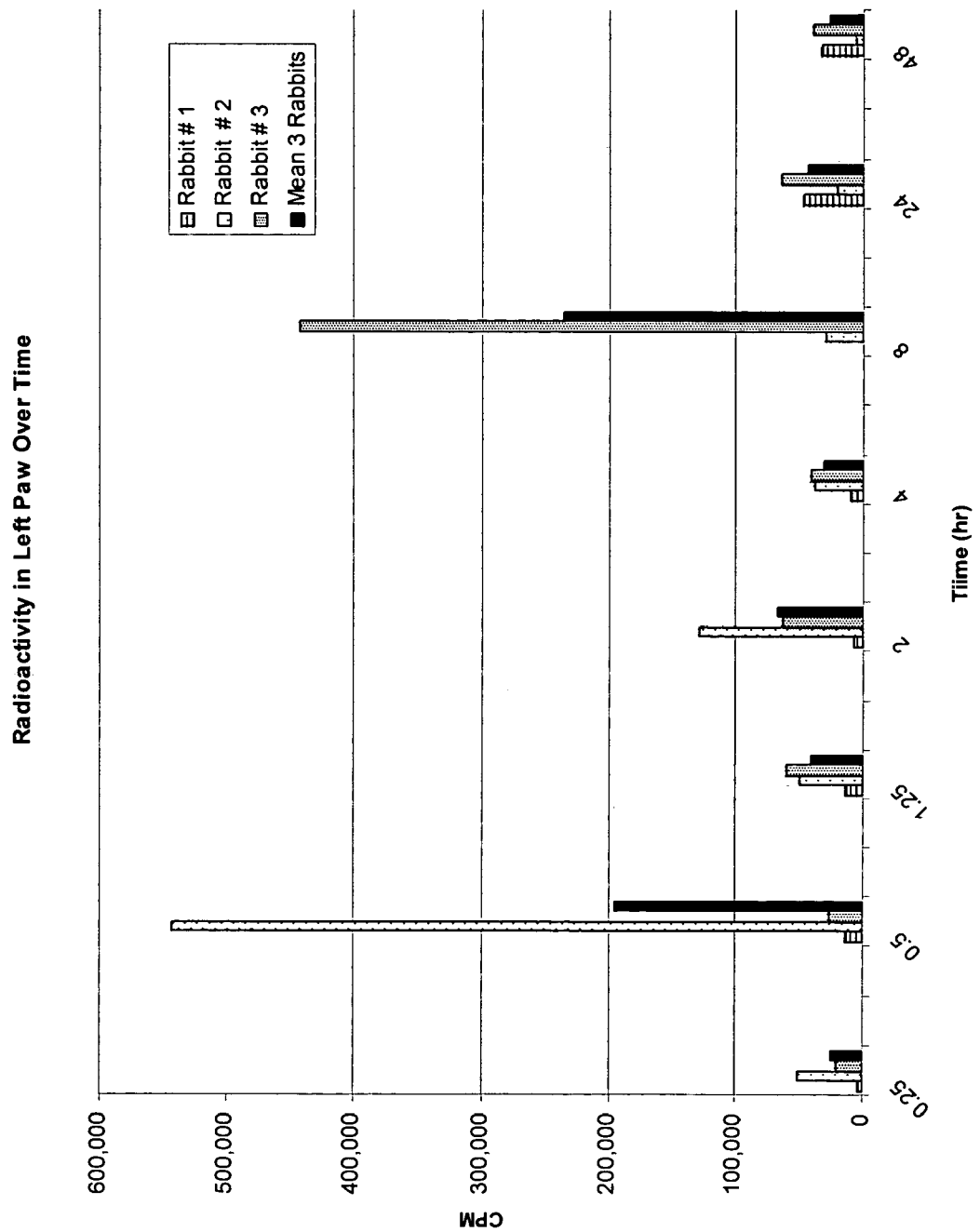
FIG. 5 illustrates the radioactivity measured in the left paw at several time periods after injection of $^{125}$I-methylene blue for each of three rabbits, and an average of the three rabbits.
Figure 6:
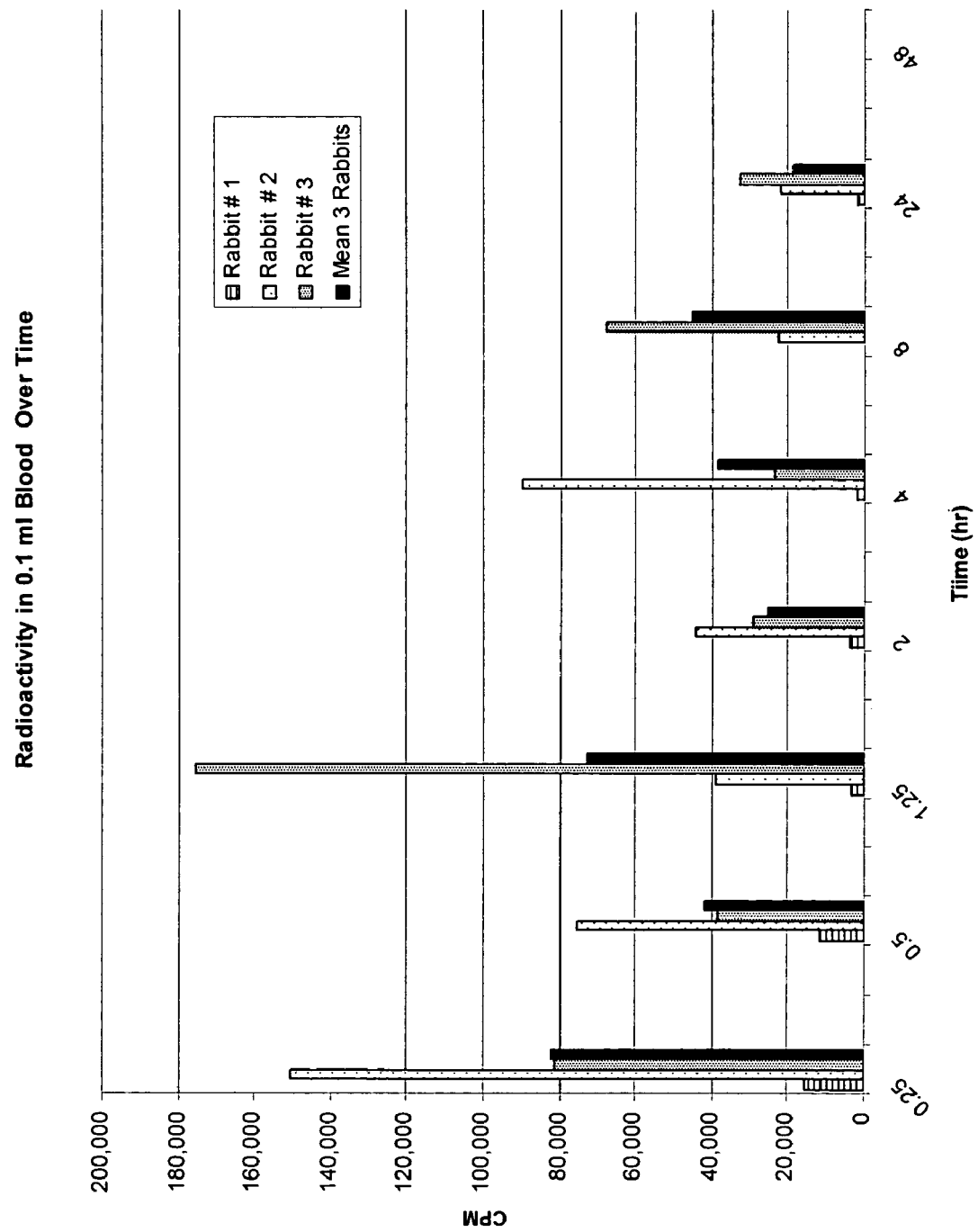
FIG. 6 illustrates the radioactivity measured in blood (0.1 ml) at several time periods after injection of $^{125}$I-methylene blue for each of three rabbits, and an average of the three rabbits.

The radioactivity measured in the right paw (the site of injection) remained steady for the entire 48 hr, with mean levels from 1.6 million CPM at 15 min to 1.4 million CPM at 48 hr. (FIG. 1) For the lymph node readings, in vivo and in vitro readings were quite similar (FIG. 2 and FIG. 3, respectively), with the highest readings at 15 min post-injection (an average of 1 million CPM). The readings slowly declined over the 48 hr to about 100,000 CPM. The background levels in the neck (FIG. 4), as well as in the left paw (FIG. 5) and blood (FIG. 6), were always less than 100,000 CPM, with the lowest reading at 48 hr. The decline over the 48 hr period represented both decay and elimination of radioactivity.

Figure 7:
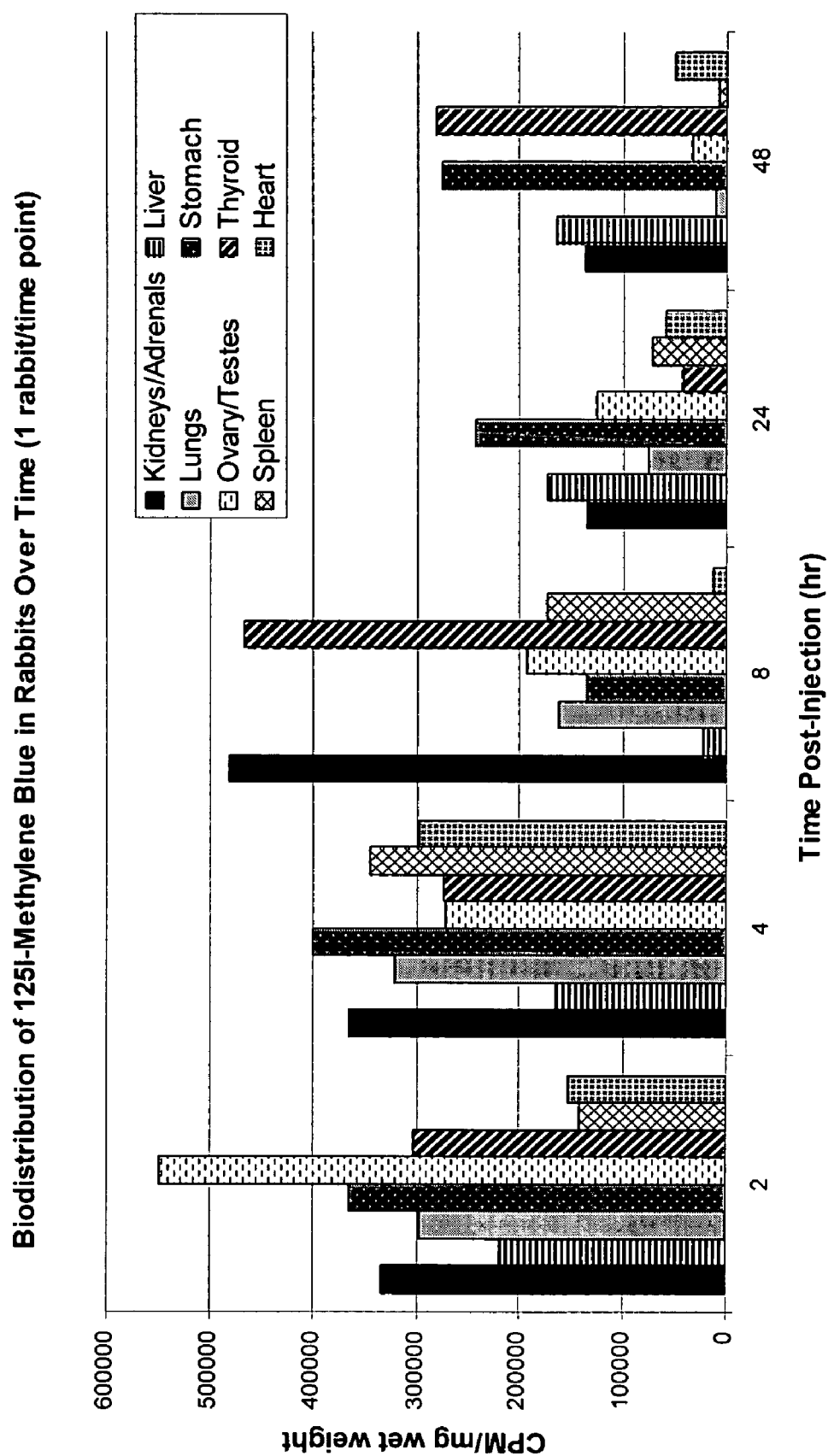
FIG. 7 illustrates the radioactivity measured in several organs at several time periods after injection of $^{125}$I-methylene blue for one rabbit at each time period.

Among the animals examined for biodistribution, no selective uptake was identified in the stomach, spleen, liver, ovary or testes, heart, lungs, or thyroid. (FIG. 6) However, a gradual increase was seen in the kidney from 2 hr to 8 hr, and then a fall at 24 hr and 48 hr. (FIG. 7). The right groin levels increased over time until 8 hr, then declined to 60,000 CPM at 48 hr. (FIG. 8) The right groin measurements indicated that the radioactive dye passed through the knee lymph node (the popliteal) into the right groin.

These results confirmed that the radiolabeled dye rapidly went to the popliteal nodes. The tissue that was blue and radioactive was nodal tissue, as confirmed by histology. (Data not shown) The radioactivity reached the node within 15 min. This is much quicker than has been reported for $^{99m}$Tc sulfur colloid, which takes from 30 min to an hour to travel to the lymph node.

EXAMPLE 2

Additional Animal Model Confirming Identification of Sentinel Lymph Node Using the One-Step Procedure To evaluate the use of the one-step procedure in a second animal model, mini-pigs (of about 75 lb) will be used. These animals are used in a training course for identification of sentinel lymph nodes offered by the Endo-Surgery Institute (Cincinnati, Ohio). The pigs will be anesthetized and then injected with a 5 cc mixture similar to that used in rabbits in Example 1. The injection will be a subcutaneous injection of the anterior thigh. After 10 min, the inguinal and groin regions of the pig will be scanned with a hand-held probe to determine regions with radioactivity ("hot" regions). An incision will be made near the hot regions to look for blue areas and discern the source of the radioactivity. Any node that is either "hot" or blue will be extracted. The location of each node will be noted. Nodal tissue will be confirmed by histochemistry.

The sentinel lymph nodes will be identified as follows: (1) Nodes that are stained blue; (2) Nodes with an afferent lymphatic channel that is stained blue; and (3) All nodes with a radioactive count that is greater than 10% of that of the sentinel lymph node having the highest count (using a hand-held gamma detector (e.g., Neoprobe; or C-Trak™, Care Wise Medical Products, Morgan Hill, Calif.). All sentinel nodes identified by the criteria listed above will be removed and stained with hematoxylin, eosin, and cytokeratin to confirm that the tissue is lymph nodal tissue. For each removed node, the presence or absence of dye and radioactivity, both in vivo and in vivo, will be recorded.

We expect these results to confirm that the radiolabeled dye rapidly goes to the major, sentinel lymph nodes, and that this technique accurately identifies the sentinel lymph node(s). It is also expected that radioactivity will reach the node within 15 min, a much quicker time than has been reported for $^{99m}$Tc sulfur colloid, which takes from 30 min to an hour to travel to the lymph node.

EXAMPLE 3

Clinical Studies of the One-Step Procedure

To evaluate the use of the one-step procedure in human patients, patients with breast cancer will be recruited under the guidelines and approval of the local Institutional Review Board. Patients will be selected who have breast cancer in either Stage I or II, and whose axillary node status is either N0 or N1. Patients will be excluded who are pregnant or nursing or who have a known sensitivity to iodine, isosulfan, lymphazurin, or methylene blue dye.

The patients will be divided into two groups, to be injected at either a peritumoral or subareolar site. Each group will be injected with a 5 cc mixture of radioactive methylene blue (0.5 cc $^{125}$I-methylene blue) and unlabeled blue dye (4.5 cc lymphazurin or methylene blue). Distribution of the injected material will be aided by either breast massage or breast compression for about 5 to about 8 min after injection.

The sentinel lymph nodes will be identified as follows: (1) Nodes that are stained blue; (2) Nodes with an afferent lymphatic channel that is stained blue; and (3) All nodes with a radioactive count that is greater than 10% of that of the sentinel lymph node having the highest count (using a hand-held gamma detector (e.g., Neoprobe; or C-Trak™, Care Wise Medical Products, Morgan Hill, Calif.). All sentinel nodes identified by the criteria listed above will be removed and stained with hematoxylin, eosin, and cytokeratin to determine the presence of malignant cells. For each removed node, the presence or absence of dye and radioactivity, both in vivo and in vivo, will be recorded.

I expect this one-step procedure will be as effective as the two-step, dual mapping procedure that is currently widely used. I expect the radiolabeled dye to travel to the lymph nodes faster than would the larger $^{99m}$Tc sulfur colloid, and thus to be more useful as during surgery.

The complete disclosures of all references cited in this specification are hereby incorporated by reference. In the event of an otherwise irreconcilable conflict, however, the present specification shall control.

I claim:

1. A method for identifying, in a mammalian patient with a solid tumor, one or more sentinel lymph nodes to which lymph from the tumor initially flows; said method comprising the steps of:
    (a) injecting radiolabeled methylene blue in or near the tumor or tumor site;
    (b) identifying as a sentinel lymph node a lymph node that, within about 20 minutes following said injecting, has accumulated a detectable fraction of the radiolabeled methylene blue, as indicated optically by the presence of the dye methylene blue, or as indicated radiologically by decay products of the radiolabel, or both; and
    (c) surgically removing the identified one or more sentinel lymph nodes.

2. A method as recited in claim 1, wherein said identifying step comprises identifying the location of one or more sentinel lymph nodes radiologically during surgery; and then further identifying the location of the one or more sentinel lymph nodes by optically locating dyed tissue during surgery, in one or more locations that had thus been indicated radiologically; and wherein said method additionally comprises the step, following said identifying, of surgically removing the identified one or more sentinel lymph nodes.

3. A method as recited in claim 1, wherein the radiolabled methylene blue is administered as an admixture with a non-radiolabeled dye; wherein the presence of the non-radiolabeled dye in a tissue may be observed optically due to the non-radiolabeled dye's visible, ultraviolet, or infrared absorption, fluorescence, luminescence, or phosphorescence; wherein the molecular weight and chemical properties of the non-radiolabeled dye are such that a detectable fraction of the non-radiolabeled dye will, following injection, travel from the tumor or the vicinity of the tumor to one or more sentinel lymph nodes within about 20 minutes.

4. A method as recited in claim 3, wherein said identifying step comprises identifying the location of one or more sentinel lymph nodes radiologically during surgery; and wherein said method additionally comprises the step, following said identifying, of surgically removing the identified one or more sentinel lymph nodes.

5. A method as recited in claim 3, wherein said identifying step comprises identifying the location of one or more sentinel lymph nodes by optically locating dyed tissue during surgery; and wherein said method additionally comprises the step, following said identifying, of surgically removing the identified one or more sentinel lymph nodes.

6. A method as recited in claim 3, wherein said identifying step comprises identifying the location of one or more sentinel lymph nodes radiologically during surgery; and then further identifying the location of the one or more sentinel lymph nodes by optically locating dyed tissue during surgery, in one or more locations that had thus been indicated radiologically; and wherein said method additionally comprises the step, following said identifying, of surgically removing the identified one or more sentinel lymph nodes.

7. A method as recited in claim 3, wherein the non-radiolabeled dye is methylene blue.

8. A method as recited in claim 3, wherein the ratio of the non-radiolabeled dye to the radiolabled methylene blue is at least about 10:1.

9. The method of claim 3, wherein the molecular weight and chemical properties of the non-radiolabeled dye are such that a detectable fraction of the dye will, following injection, travel from the injection site to one or more sentinel lymph nodes within about 15 minutes.

10. The method of claim 3, wherein the molecular weight and chemical properties of the non-radiolabeled dye are such that a detectable fraction of the dye will, following injection, travel from the injection site to one or more sentinel lymph nodes within about 10 minutes.

11. The method of claim 1, wherein the radiolabled methylene blue is $^{125}$I-methylene blue.

12. The method of claim 3, wherein the radiolabled methylene blue is 125I-methylene blue and the non-radiolabeled dye is isosulfan blue.

13. The method of claim 1, wherein the tumor is selected from the group consisting of melanoma, breast cancer, head and neck cancer, lung cancer, bladder cancer, neuroendocrine cancer, squamous carcinoma, prostate cancer, gastric cancer, cervical cancer, vulvar cancer, thyroid cancer, pancreatic cancer, renal cancer, esophageal cancer, rectal cancer, penile cancer, lymphoma, multiple myloma, Merkel cell tumors, ovarian cancer, and colorectal cancer.

14. The method of claim 1, wherein the tumor is breast cancer.

15. The method of claim 1, wherein the tumor is melanoma.

16. The method of claim 1 wherein the radiolabel emits particles with an energy less than about 300 keV.

17. The method of claim 1 wherein the radiolabel emits particles with an energy less than about 150 keV.

18. The method of claim 1 wherein the radiolabel emits particles with an energy less than about 50 keV.

19. The method of claim 1, wherein the radiolabel is an isotope of an element selected from the group consisting of Tc, Re, Mn, Fe, Se, Co, Ni, Zn, Cd, Mo, W, Cu, Ag, Au, Tl, Hg, Cr, Rh, B, I, Cl, F, At, Y, Lu, Gd, Ga, Ho, In, Sm and Yb.

20. The method of claim 1, wherein the radiolabel is selected from the group consisting of $^{125}$I, $^{111}$In, $^{75}$Se, $^{57}$Co, $^{124}$I, $^{90}$Y, $^{68}$Ga, $^{123}$I, $^{124}$I, $^{18}$F, $^{131}$I, $^{99m}$Tc, $^{169}$Yb, $^{186}$Re $^{188}$Re, $^{211}$At, $^{77}$Br, $^{67}$Ga, $^{86}$Y, $^{193}$Pt, $^{195m}$Pt, and $^{201}$Tl.

21. The method of claim 1, wherein the radiolabel is $^{125}$I.

22. The method of claim 3, wherein the non-radiolabeled dye is selected from the group consisting of patent blue dye, isosulfan blue, methylene blue, fluorescein, tartrazine, iodocyanine green, rose Bengal, and congo red.

* * * * *